Feb. 1, 1966 L. LENS Plant Pat. 2,592
ROSE PLANT
Filed Oct. 21, 1964
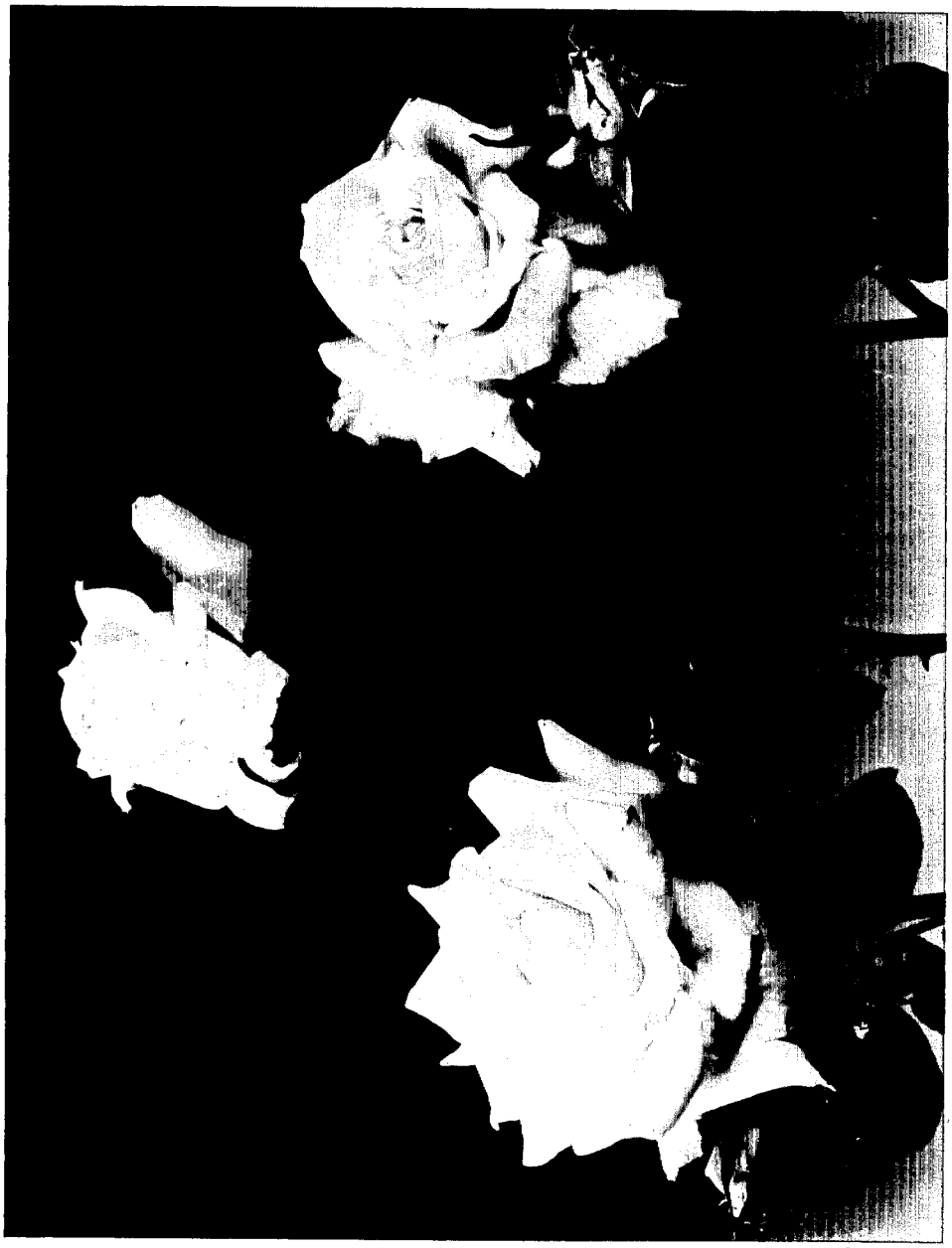
Inventor.
Louis Lens
By: Robb & Robb
Attorneys.

United States Patent Office

Plant Pat. 2,592
Patented Feb. 1, 1966

2,592
ROSE PLANT

Louis Lens, Wavre-Notre-Dame, Belgium, assignor to Armstrong Nurseries, Inc., Ontario, Calif., a corporation of California Filed Oct. 21, 1964, Ser. No. 405,633
Claims priority, application Belgium, Oct. 30, 1963, 639,398
1 Claim. (Cl. Plt.—14)

The present invention relates to a new and distinct variety of rose plant of the hydbrid tea class, which was originated by me by crossing the variety "Queen Elizabeth" (U.S. Plant Patent No. 1259) with the variety "White Butterfly" (U.S. Plant Patent No. 1,337), the former being the seed parent, and the latter being the pollen parent.

The primary objective of this breeding was to produce a new and improved rose variety of the hybrid tea class which bears white flowers, combined with strong plant growth, and which is especially suitable for greenhouse forcing use, as well as for outdoor garden use. This objective was fully achieved, along with other desirable improvements, as evidenced by the following unique combination of characteristics which are outstanding in the new variety and which distinguish it from its parents, as well as from all other varieties of which I am aware:

(1) A vigorous and upright habit of growth approaching that of the parent variety "Queen Elizabeth";

(2) Large, attractive and mildew resistant foliage comparable to that of the variety "Queen Elizabeth";

(3) An elegant bud form ranging from pointed to urn-shaped, which opens well under nearly all connections;

(4) Abundant production of double, white flowers which are borne both singly and in small clusters;

(5) Very long-lasting flower qualities, both as cut flowers and on the plant; and (6) An ability to force well under glass for cut flowers.

In comparison with its seed parent, "Queen Elizabeth," the new variety primarily differs therefrom by bearing flowers of white color, while those of this parent variety are pink.

As compared with its pollen parent, "White Butterfly," the new variety is differentiated therefrom by its more vigorous plant habit, more mildew resistant foliage, and greater flower petalage, averaging from 5 to 10 more petals for flower.

Asexual reproduction of my new variety by budding, as performed at Wavre-Notre-Dame, Belgium, and also at Ontario, California, U.S.A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated (W) and Robert Ridgway's Color Standards and Nomenclature (hereinafter abbreviated (R)), as indicated:

Type: Bush; greenhouse and outdoor; seedling; for cut flowers and for garden decoration.

Class: Hybrid tea.
Breeding: Seedling.
*Seed parent.*—"Queen Elizabeth."
*Pollen parent.*—"White Elizabeth."
Propagation: Holds its distinguishing characteristics through succeeding propagations by budding.

*Flower*

Locality where grown and observed: Ontario, California, U.S.A.
Flowers Borne: Sometimes singly and sometimes from 2 to 5 flowers to stem; in irregular clusters; on stems of medium length and normal strength.
Quantity of bloom: Abundant, both outdoors and in greenhouse.
Continuity: Nearly continuous during growing season.
Fragrance: Slight.
Bud:
*Peduncle.*—From short to average length; average caliper; erect; usually smooth; with few hairs. Color—near Grape Green, Plate XLI (R).
*Before calyx breaks.*—Size—from small to medium. Form—from short to medium length; ovoid.
*As calyx breaks.*—Color—near Primrose Yellow, Plate 601/2, page 65 (W), with area exposed longer to sun overlaid with near Empire Rose, Plate 0621/2, page 183 (W).
*Sepals.*—Margins of alternate sepals lined with fine wooly tomentum, with margins of others having from none to few small stipitate glands and small slender foliaceous parts.
*As first petal opens.*—Size—from small to average. Form—medium length; ovoid. Color: Outside—between white and near Uranium Green, Plate 63/3, page 63 (W), blending with near Uranium Green, Plate 63/3, page 63 (W) toward base of petal; inside—between white and near Dresden Yellow, Plate 64/3, page 64 (W), blending with near Dresden Yellow, Plate 64/3, page 64 (W) toward base of petal.
*Opening.*—Opens up well; is not prevented from opening by cold, hot, wet or dry weather.
Bloom:
*Size (when fully open).*—Medium; from 3½ inches to 4 inches.
*Petalage.*—Double; from 30 to 38 petals, plus 4 to 10 petaloids; arranged irregularly.
*Form.*—High-centered at first, but becoming from cupped to high-centered; petals being at first somewhat tightly cupped, with tips reflexed outward, but later becoming more loosely cupped, with tips reflexed outward at maturity; outside and intermediate petals of both newly opened and three-days open flowers usually reflexed outward both along edges and apex of petal; outside petals usually strongly reflexed outward.
Petals:
*Texture.*—Medium thickness.
*Appearance.*—Inside—satiny. Outside—satiny.
*Shape.*—Outside—between round and broadly obovate, with apex flat and sometimes with one or two notches. Intermediate—obovate, with apex from rounded to flat and sometimes with one or two notches. Inside—narrowly obovate; irregular; with apex rounded.

This description of a newly opened flower was made from a rose grown outdoors during the month of June at Ontario, California, U.S.A.:

*Color.*—Outer petal: Outside surface — between white and near Primrose Yellow, Plate 601/3, page 65 (W), blending with near Uranium Green, Plate 63/3, page 63 (W) toward base of petal; inside surface—between white and near Primrose Yellow, Plate 601/3, page 65 (W), blending with near Uranium Green, Plate 63/3, page 63 (W) toward base of petals. Intermediate petal: Outside surface—between white and near Primrose Yellow, Plate 601/3, page 65 (W), blending with near Uranium Green, Plate 63/3, page 63 (W) toward base of petal; inside surface—between white and near Primrose Yellow, Plate 601/3, page 65 (W), blending with near Uranium Green, Plate 63/3, page 63 (W) toward base of petal. Inner petal: Outside surface—near Mimosa Yellow, Plate 602/3, page 143 (W), blending with near Primrose Yellow, Plate 601/3, page 65 (W) toward base of petal; inside surface—near Mimosa Yellow, Plate 602/3, page 143 (W), blending with near Primrose Yellow, Plate 601/3, page 65 (W) toward base of petal.

This description was made from a rose that was open for three days outdoors during the month of June at Ontario, California, U.S.A.:

*Color.*—Outer petal: Outside surface — between white and near Chartreuse Green, Plate 663/3, page 90 (W), blending with near Primrose Yellow, Plate 601/3, page 65 (W) toward base of petal; inside surface—between white and near Chartreuse Green, Plate 663/3, page 90 (W), blending with near Primrose Yellow, Plate 601/3, page 65 (W) toward base of petal. Inner petal: Outside surface—between white and near Chartreuse Green, Plate 663/3, page 90 (W), blending with near Dresden Yellow, Plate 64/3, page 64 (W) toward base of petal; inside surface—between white and near Chartreuse Green, Plate 663/3, page 90 (W), blending with near Dresden Yellow, Plate 64/3, page 64 (W) toward base of petal.

*General color effect.*—Newly opened flower—between white and near Mimosa Yellow, Plate 602/3, page 143 (W), with center of flower sometimes blending with near Empire Yellow, Plate 603/3, page 66 (W). 3-days open—between white and near Chartreuse Green, Plate 663/3, page 90 (W), with center of flower between white and near Empire Yellow, Plate 603/3, page 66 (W).

*Behavior.*—Drop off cleanly; not particularly affected by cold, hot, wet or dry weather.

*Flower longevity.*—On bush in garden—4 or 5 days in June. Cut roses grown outdoors and kept at living room temperatures—from 4 to 6 days in June.

*Reproductive organs*

Stamens: From few to average number; arranged regularly about pistils; a few mixed with petaloids.

Filaments: From short to medium length (from 4 to 10 mm. long); most with anthers. Color—near Dresden Yellow, Plate 64/2, page 64 (W).

Anthers: From small to medium size; all open approximately at once. Color: Upper side—margins near Cadmium Orange, Plate 8/2, page 8 (W), with remainder near Dresden Yellow, Plate 64/3, page 64 (W); under side—margins near Cadmium Orange, Plate 8/2, page 8 (W), with remainder near Dresden Yellow, Plate 64/3, page 64 (W).

Pollen: Moderate abundance. Color—near Cadmium Orange, Plate 8/1, page 8 (W).

Pistils: Average number (approximately 50).

Styles: Uneven, from short to average length; from thin to average caliper: bunched. Color—upper third of style near Scarlet, Plate 19/2, page 19 (W), with remainder near Primrose Yellow, Plate 601/2, page 65 (W).

Stigma: Color—near Salmon, Plate 412, page 123 (W).

Ovaries: Usually all enclosed in calyx.

Hips: None observed.

Sepals: Permanent due to fact that receptacle and sepals dry up before sepals might otherwise drop; medium length; usually straight. Color: Inside—near Light Grape, Green, Plate XLI (R); outside—near Absinthe Green, Plate XXXI (R), sometimes overlaid with near Deep Corinthian Red, Plate XXVII (R).

Seeds: None observed.

*Plant*

Foliage:

*Leaves.*—Compound of usually 3 to 5 leaflets; abundant; large; leathery; glossy.

*Leaflets.*—Shape—between round and oval. Apex—acute. Base—round. Margin—simply serrate.

*Color.*—Mature: Upper surface — between Cress Green, Plate XXXI (R) and Dark Dull Yellow-Green, Plate XXXII (R); under surface—near Chromium Green, Plate XXXII (R). Young: Upper surface—near Rainette Green, Plate XXXI (R), with edges of leaflets overlaid with near Indian Red, Plate XXVII (R); under surface—near Mignonette Green, Plate XXXI (R), with edges of leaflets overlaid with near Indian Red, Plate XXVII (R).

*Rachis (the supporting stem of the compound leaf).*—Average size. Upper surface—grooved; with from none to few small stipitate glands on edges. Under surface—smooth; with from none to few stipitate glands and from none to few small prickles.

*Stipules.*—From short to medium length; from medium width to wide; with short points turning out at an angle of more than 45°.

*Disease resistance.*—Better than average resistance to mildew, as determined from comparison with other varieties grown under comparable cultural conditions at Ontario, California, U.S.A.

Growth:

*Habit.*—Upright; much-branched.

*Growth.*—Vigorous.

*Canes.*—Medium caliper.

*Main stems.*—Color—near Light Elm Green, Plate XVII (R). Large prickles—from few to several; medium length; almost straight; with base of medium length; color—near Cinnamon, Plate XXIX (R). Small prickles—from none to few; color—near Cinnamon, Plate XXIX (R). Hairs—none.

*Branches.*—Color—near Chromium Green, Plate XXXII (R). Large prickles—from few to several medium length; almost straight; with base of medium length; color—near Pecan Brown, Plate XXVIII (R). Small prickles—from few to several; color—near Pecan Brown, Plate XXVIII (R). Hairs—none.

*New shoots.*—Color—near Absinthe Green, Plate XXXI (R), with side exposed to sun overlaid with near Buffy Olive, Plate XXX (R). Large prickles—few; from short to medium length; almost straight; with base of medium length; color—near Deep Corinthian Red, Plate XXVII (R). Small prickles—from several to many; color—near Deep Corinthian Red, Plate XXVII (R). Hairs—none.

I claim:

A new and distinct variety of rose plant of the hybrid tea class, substantially as herein shown and described, characterized particularly as to novelty by the unique combination of a vigorous and upright habit of growth approaching that of the parent variety "Queen Elizabeth," large, attractive and mildew resistant foliage comparable to that of the variety "Queen Elizabeth," an elegant bud form ranging from pointed to urn-shaped, which opens well under nearly all conditions, abundant production of double, white flowers which are borne both singly and in small clusters, very long-lasting flower qualities, both as cut flowers and on the plant, and an ability to force well under glass for cut flowers.

No references cited.

ABRAHAM G. STONE, *Primary Examiner.*

R. E. BAGWILL, *Assistant Examiner.*